United States Patent [19]

Mileikowsky

[11] Patent Number: 4,705,955
[45] Date of Patent: Nov. 10, 1987

[54] RADIATION THERAPY FOR CANCER PATIENTS

[76] Inventor: Curt Mileikowsky, c/o Instrument AB Scanditronix, Box 7412, 103 91 Stockholm, Sweden

[21] Appl. No.: 719,226

[22] Filed: Apr. 2, 1985

[51] Int. Cl.$^4$ .................... G01N 21/00; H01J 37/00
[52] U.S. Cl. .................. 250/492.1; 250/492.3; 250/491.1; 378/196; 378/205
[58] Field of Search ............... 250/491.1, 492.1, 492.3; 376/65, 196, 205, 112

[56] References Cited

U.S. PATENT DOCUMENTS

| | | | |
|---|---|---|---|
| 1,333,349 | 3/1920 | Stirckler | 378/196 |
| 2,353,145 | 7/1944 | Chamberlain | 378/196 |
| 3,670,163 | 6/1972 | Lojus | 378/196 |
| 3,757,118 | 9/1973 | Hodge et al. | 250/492.3 |
| 3,852,611 | 12/1974 | Cesar | 378/196 |
| 3,925,676 | 12/1975 | Bigham et al. | 376/112 |
| 4,230,129 | 10/1980 | Le Veen | 378/65 |
| 4,242,587 | 12/1980 | Lescrenier | 378/205 |
| 4,256,966 | 3/1981 | Heinz | 250/491.1 |
| 4,296,329 | 10/1981 | Mirabella | 250/491.1 |

Primary Examiner—Bruce C. Anderson
Attorney, Agent, or Firm—Lewis H. Eslinger

[57] ABSTRACT

Apparatus for irradiating a patient comprises a source of a radiation beam directed along a radiation axis. The source is mounted for pivotable movement about a first horizontal axis substantially normal to the radiation axis, whereby the beam is capable of an angular scan in a vertical plane. In a preferred embodiment the apparatus is positioned so that the midplane between the pole surfaces substantially includes the first horizontal axis. A table is adapted to support a patient to be irradiated. A suspension unit mounts the table for arcuate movement to any of a plurality of positions angularly spaced about the first horizontal axis and for pivoting movement about a second horizontal axis displaced from and substantially parallel to the first horizontal axis. The suspension unit maintains the second horizontal axis in substantially intersecting relation to the radiation axis in each such position while maintaining a fixed angular position of the table with respect to the environment.

57 Claims, 15 Drawing Figures

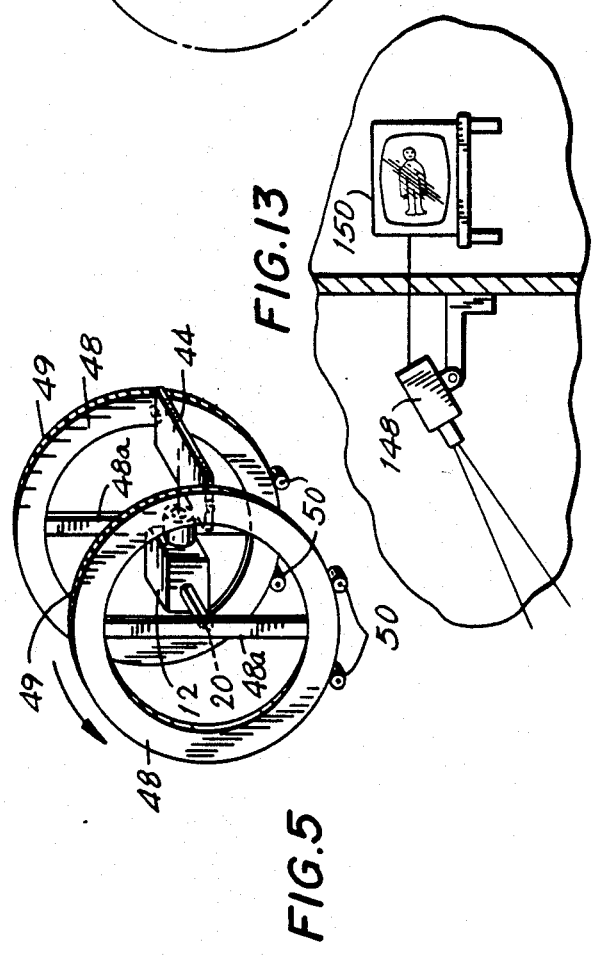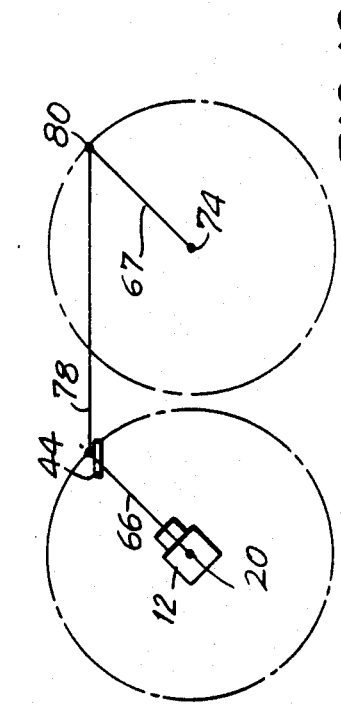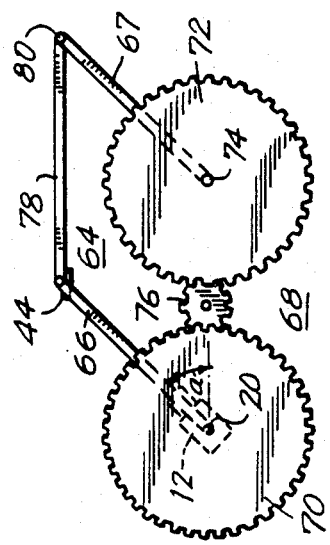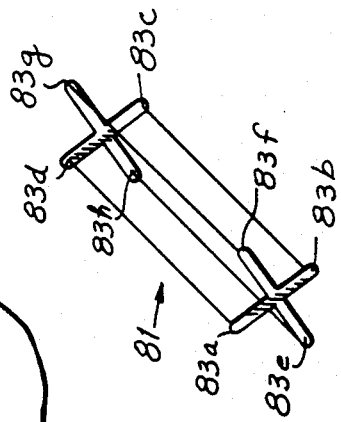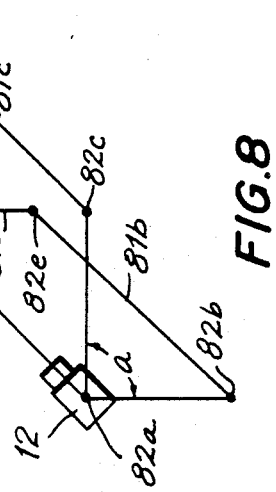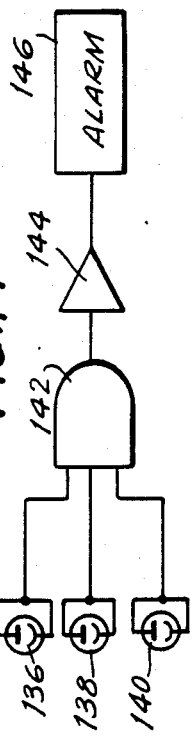

RADIATION THERAPY FOR CANCER PATIENTS

BACKGROUND OF THE INVENTION

1. Field of the Invention

This invention relates to a method and apparatus for irradiating a patient and, more particularly, to a novel and highly-effective method and apparatus for radiation therapy for cancer patients.

2. Description of the Prior Art

Cancer cells can be weakened and ultimately killed by bombardment with certain kinds of radiation, and radiation therapy is an important treatment for cancer. A problem with radiation therapy is that the radiation that kills the cancer cells also injures and may kill normal cells, so that the patient's body is damaged by the treatment.

To minimize this problem, it is conventional to irradiate a patient at different angles. For example, a patient may be irradiated for three or four minutes per session in a number of sessions spread over a period of weeks, the radiation being directed in each session along a different radiation axis. The tumor is made the "pivot" or "fulcrum" of the radiation beam as it were, so that each radiation dose passes through the tumor, the cells of which will be heavily damaged and possibly killed. Normal cells, on the other hand, receive much smaller radiation doses, from which they are expected to recover.

Because of the damage that radiation is capable of doing to normal cells, it is desirable to ascertain the position of the tumor within the body to an accuracy of a millimeter or less. It is therefore desirable that the patient assume a standard position so that the effects of gravity on the position of internal organs is minimized. The standard position for radiation therapy is typically the supine position, although the prone position and other recumbent positions can also be employed. The patient must remain quite still during the radiation therapy for a period that may for example be three or four minutes.

The radiation may consist of charged particles, neutrons or photons. Neutrons have been found particularly efficacious for the treatment of certain types of prostatic cancer. In any case, one type of machine constituting a radiation source comprises a floor-mounted acceleration chamber for accelerating charged particles and a gantry connected thereto and having the shape of a gooseneck. The gantry can be swivelled about a horizontal axis so that the radiation emitted through the "mouth" of the gooseneck is directed substantially radially inward towards the patient from any selected position in an arc concentric with a point in the patient. This makes it possible to irradiate a tumor from various angles, thereby possibly killing the cancer cells while sparing the surrounding normal cells.

Of course, the gantry is massive, because it must contain large coils and heavy magnets for bending the path of the charged particles as they travel through the gooseneck. Consequently, the gantry normally requires an equally massive counterweight to facilitate its swivelling movement. If neutrons are to be generated, the gantry must also contain a target, which in this machine design must be located substantially in the mouth of the gantry, since the direction of travel of a neutron can not be changed by a magnetic or electrostatic field and is determined by the dynamics of the collision between the charged particles and the target.

In another type of machine the acceleration chamber itself is mounted in a gantry, which can be gooseneck-shaped or a drum, etc., and moves around the patient in order to irradiate the patient from various angles. This also requires a counterweight, since the machine is massive.

The machine may be a cyclotron, synchro-cyclotron, synchrotron, or microtron. Also, the coils of some such machines for generating the magnetic field may be superconducting or not. If superconducting, the size and weight of the machine is significantly reduced.

Even in the most favorable case, however, the total mass of the machine is measured in tens of tons and the cost in millions of dollars (1985 prices). In addition, such a bulky and massive installation requires a substantial amount of floor space and a substantial ceiling height and may require strengthening of building supports, etc., so that the total cost of the installation substantially exceeds the purchase price of the machine itself.

Examples of the prior art include U.S. Pat. Nos. 3,925,676, to Bigham to Nunan 4,112,306, and to Rautenbach 4,139,777. The Bigham and Nunan patents disclose cyclotrons, the coils of which are respectively superconducting and nonsuperconducting, as a source of neutrons for medical therapy. The cyclotrons are moved orbitally about a stationary patient, whereby the patient can be irradiated from different angles.

The Rautenbach patent discloses a linear rail whereby a cyclotron may be rolled so that it projects a beam in different directions; means whereby a beam of charged particles can be extracted at different circumferential points of an accelerator chamber; and a pivot beam whereby a cyclotron can be moved in an orbital path about a horizontal pivot axis in a manner such that the radiation axis of a neutron beam intersects the horizontal pivot axis, where the patient is positioned.

All of these structures are massive and ideally require equally massive counterweights to facilitate the described orbital movements of the radiation sources. This results in a substantial cost not only for the installation itself but also for space rental, building strengthening, etc., as indicated above.

OBJECTS AND SUMMARY OF THE INVENTION

An object of the invention is to remedy the problems outlined above of conventional apparatus for irradiating a patient and, in particular, to provide apparatus for irradiating a patient, the apparatus being designed so that it weighs and costs significantly less than conventional apparatus.

Another object of the invention is to provide apparatus for irradiating a patient that can employ a cyclotron as the radiation source (whether or not the coils for generating the magnetic field are superconducting), a synchro-cyclotron having superconducting coils for generating the magnetic field, a synchrotron having superconducting coils for generating the magnetic field, or a microtron.

Another object of the invention is to provide apparatus that requires little or no counterweight yet which is readily adapted for movement to irradiate a patient accurately from different angles.

Another object of the invention is to provide apparatus for irradiating a patient that is easy and inexpensive to service.

Another object of the invention is to provide a method that facilitates the precise positioning of a patient so that a tumor in the patient is accurately positioned with respect to an axis of radiation from a radiation source and can be irradiated from different angles.

Another object of the invention is to provide a method that makes it possible to irradiate a patient from different angles in a single treatment session.

In accordance with one aspect of the invention, apparatus is provided for irradiating a patient and comprising: a source of a radiation beam directed along a radiation axis; means mounting the source for pivotable movement about a first horizontal axis substantially normal to the radiation axis, whereby the beam is capable of an angular scan in a vertical plane; table means adapted to support a patient to be irradiated; and suspension means mounting the table means for arcuate movement to any of a plurality of positions angularly spaced about the first horizontal axis and for pivoting movement about a second horizontal axis displaced from and substantially parallel to the first horizontal axis, the suspension means maintaining the second horizontal axis in substantially intersecting relation to the radiation axis in each of the positions while maintaining a fixed angular position of the table means with respect to the environment.

In accordance with an independent aspect of the invention, a method of irradiating a tumor is provided comprising the steps of: providing a source of a radiation beam directed along a radiation axis; providing a table having a substantially flat upper surface for supporting a patient; positioning a patient on the surface so that the radiation axis intersects the tumor at a first angle; irradiating the tumor at the first angle; rotating the radiation axis about a first horizontal axis and simultaneous moving the table so that the radiation axis intersects the tumor at a second angle while pivoting the table about a second horizontal axis displaced from and substantially parallel to the first horizontal axis to maintain the surface substantially level; and irradiating the tumor at the second angle.

BRIEF DESCRIPTION OF THE DRAWINGS

A better understanding of the invention can be gained from the following detailed description of the preferred embodiments thereof, in conjunction with the appended figures of the drawings, wherein like reference numbers indicate like parts, and wherein:

FIG. 5 is a perspective view of another embodiment of apparatus constructed in accordance with the invention;

FIG. 7 is a schematic view in side elevation of another embodiment of apparatus constructed in accordance with the invention;

FIGS. 8, 9 and 10 are schematic views of modifications of the apparatus of FIG. 7;

FIG. 13 is a schematic view in elevation of monitoring apparatus useful in accordance with the invention; and FIG. 14 is a schematic representation of indicator apparatus useful in accordance with the invention.

DESCRIPTION OF THE PREFERRED EMBODIMENTS

Figure 1:
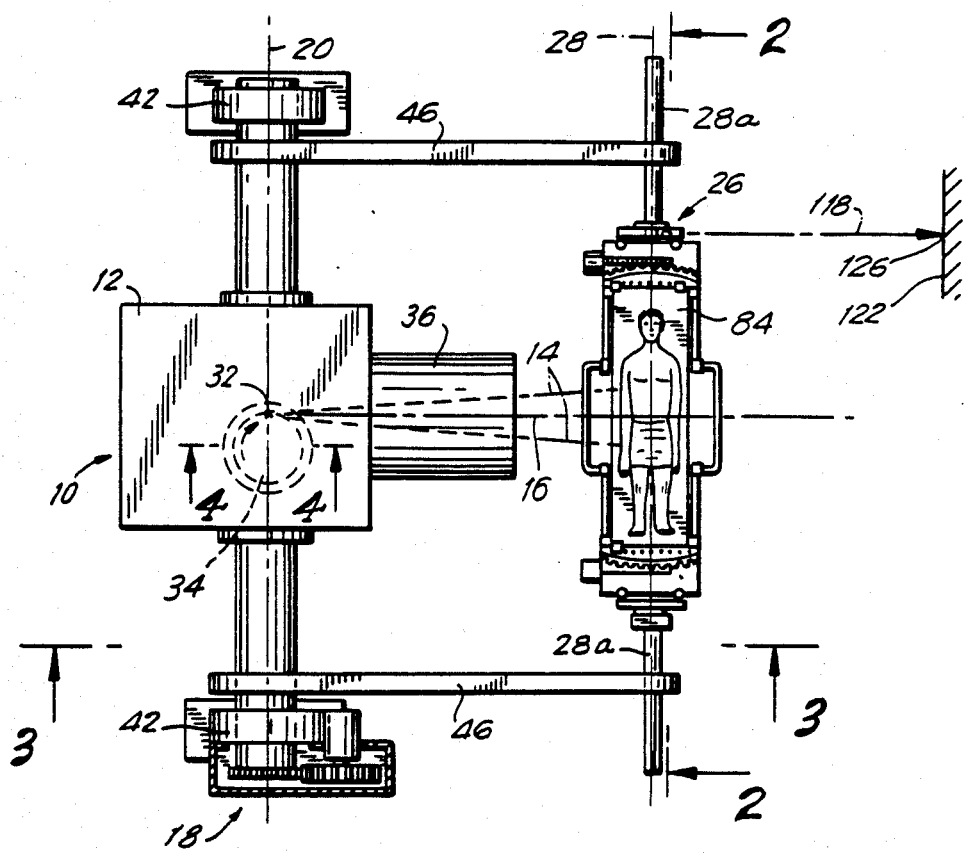
FIG. 1 is a top plan view of a first embodiment of apparatus constructed in accordance with the invention.

FIG. 1 shows apparatus 10 for irradiating a patient. The apparatus comprises a source 12 of a radiation beam 14 directed along a radiation axis 16. Means 18 is provided for mounting the source 12 for pivotable movement about a first horizontal axis 20 which intersects said source, is stationary with respect to the apparatus 10, and extends in a direction substantially normal to the radiation axis 16, whereby the beam 14 is capable of an angular scan in a vertical plane.

Figure 2:
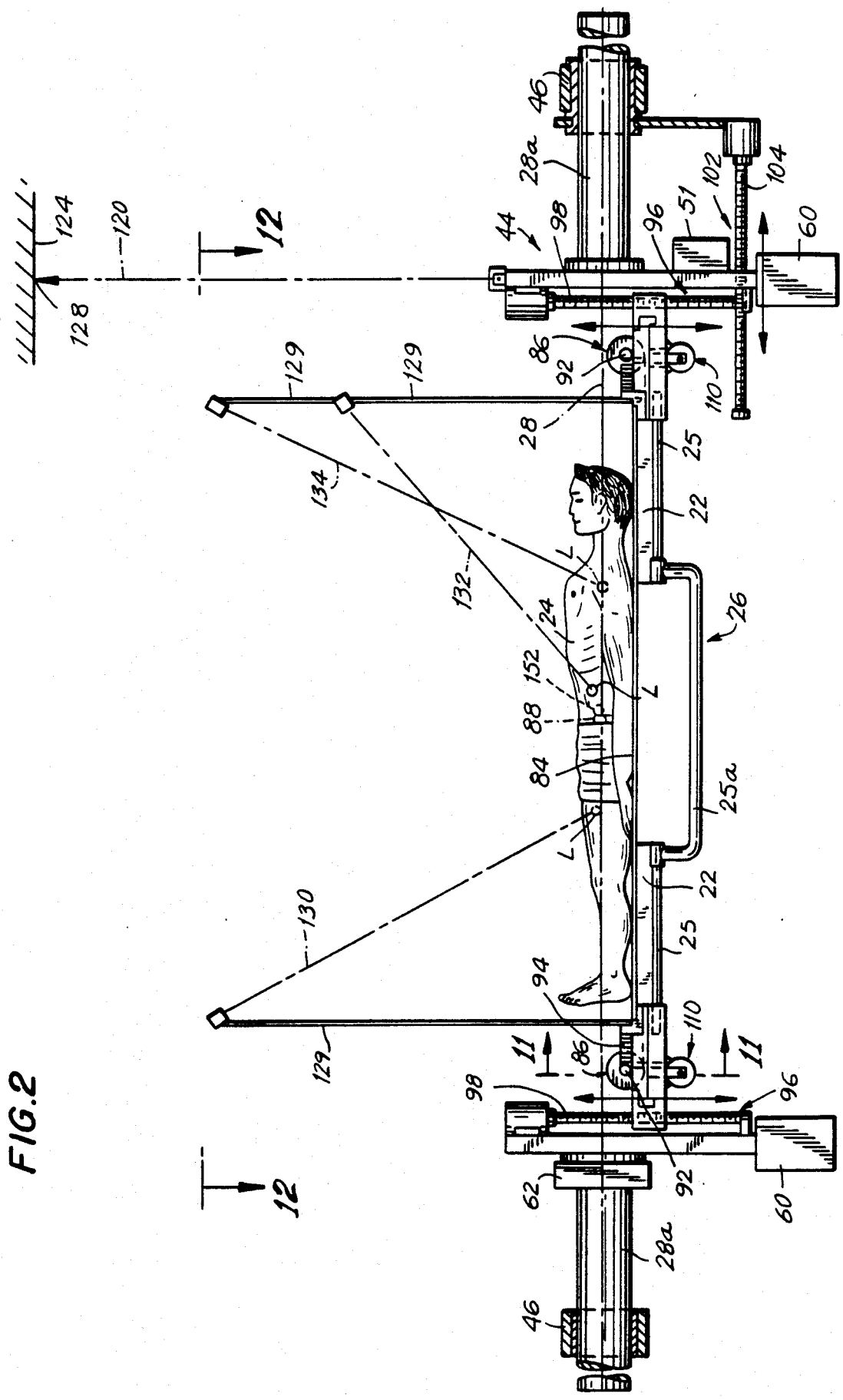
FIG. 2 is a view taken along the line 2—2 of FIG. 1 and looking in the direction of the arrows.

Means such as a table 22 (FIG. 2) is adapted to support a patient 24 to be irradiated. The table 22 is made of a material that is not readily made dangerously radioactive and that can be penetrated by the radiation used, so that the patient can be irradiated if necessary from below the level of the table 22. The table 22 is quite thin in the vertical dimension in and near the plane in which the radiation axis 16 rotates. Reinforcing structures 25, conventional per se, extend along the length of the table 22 at each side for reinforcement. Each reinforcing structure 25 has a U-shaped portion 25a, and the reinforcing structures 25, on at least the respective portions 25a thereof, can be pivoted about respective axes parallel to the length of the table 22. This enables the portions 25a to be moved so as to avoid intercepting the radiation beam at certain beam angles. The structures 25, or possibly only the portions 25a thereof, may comprise lengths of pipe.

Means such as a suspension unit 26 (FIGS. 1 and 3) mounts the table 22 for arcuate movement to any of a plurality of positions angularly spaced about the first horizontal axis 20 and for pivoting movement about a second horizontal axis 28 displaced from and substantially parallel to the first horizontal axis 20. A support shaft 28a is coaxial with the axis 28. The suspension 26 maintains the second horizontal axis 28 in substantially intersecting relation to the radiation axis 16 in each of the angular positions while maintaining a fixed angular position of the table 22 with respect to the environment.

Figures 3, 3A:
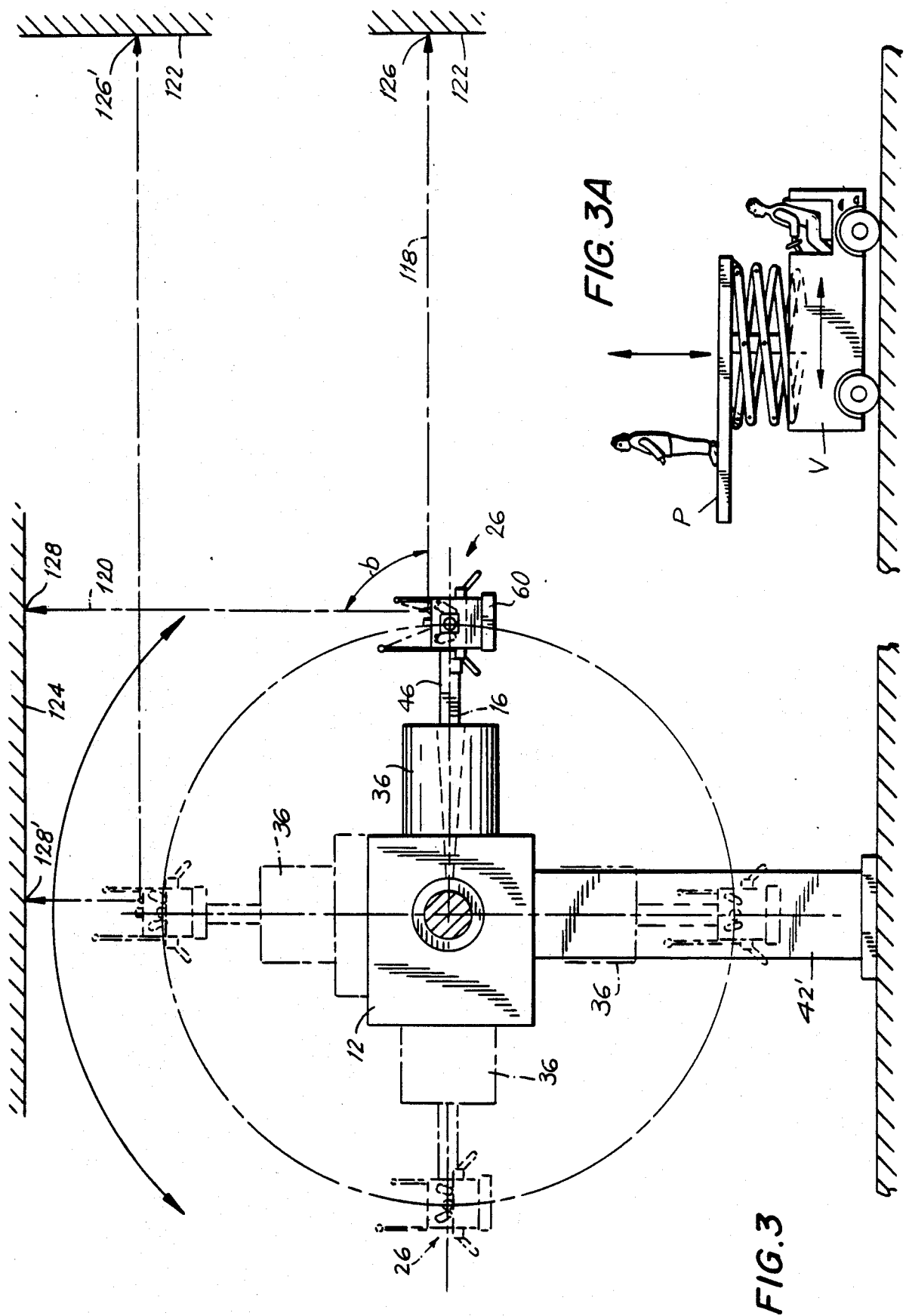
FIG. 3 is a view taken along the line 3—3 of FIG. 1 and looking in the direction of the arrows.
FIG. 3A is a view in side elevation of a vehicle useful in retrieving a patient from the apparatus of FIG. 1 in the event of power failure with the patient in an elevated position.

FIG. 3 shows a first of the angular positions in solid outline and shows three other angular positions in phantom outline, successive positions being spaced apart from one another at intervals of 90°. While four angular positions about the first horizontal axis 20 are shown, the apparatus can be oriented so that the radiation axis 16 assumes any angular position whatsoever about the first horizontal axis 20 in order to irradiate a tumor from any angle.

Figure 4:
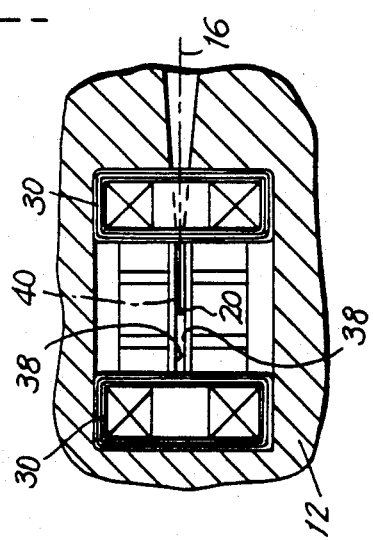
FIG. 4 is a view taken along the line 4—4 of FIG. 1 and looking in the direction of the arrows.

The source 12 may typically be a cyclotron. Preferably, in order to minimize the weight of the source, it has superconducting coils 30 (FIG. 4) for generating the magnetic field. If the source is a cyclotron, it comprises an internal target 32 and means including an acceleration chamber 34 for accelerating charged particles. The apparatus 10 is positioned so that the first horizontal axis 20, the internal target 32, and the radiation axis 16 intersect substantially at a point, and so that the axes 20 and 16 form a right angle. The charged particles collide with the internal target 32 substantially at that point and just as their path of movement becomes tangent to the radiation axis 16. The internal target 32 may for example comprise beryllium, and neutrons ejected therefrom by the collision of the charged particles with the internal target 32 have a direction of movement that depends on the dynamics of the collision. Generally, this direction will have a distribution centered on the radiation axis 16. A shield or collimator 36 is formed with an aperture that admits neutrons having a direction of movement which forms an angle with respect to the radiation axis 16 within a given outer limit and excludes neutrons having a direction of movement which forms an angle with respect to the radiation axis 16 beyond that limit. Thus the radiation beam 14 is for example conical, and the cone angle or half-angle is adjustable in accordance with the geometry of the shield 36. The beam 14 need not be circularly conical and may have any desired cross-sectional shape.

As an alternative to a cyclotron, the source 12 may comprise a synchro-cyclotron having superconducting coils for generating the magnetic field. As another alternative, the source 12 may comprise a synchrotron having superconducting coils for generating the magnetic field.

In the case of both the synchro-cyclotron and the synchrotron, the coils for generating the magnetic field should be superconducting, since without such a feature the source is so massive that it is preferable that it be stationary rather than mounted for pivoting movement about the first horizontal axis 20.

As another alternative, the source may comprise a microtron. A target may be bombarded by the electrons in order to produce high-energy photons for use in photon therapy.

Any of the sources employed in accordance with the invention may include spaced-apart pole surfaces 38 (FIG. 4) for generating a magnetic field. Preferably, the apparatus is positioned so that the midplane 40 (FIG. 4) between the pole surfaces 38 substantially includes the first horizontal axis 20. Since the magnets and coils are symmetrically positioned on opposite sides of this midplane, the center of mass of the cyclotron can be made to lie very close to the first horizontal axis 20. Since the cyclotron far outweighs the suspension unit 26 (whether or not a patient is supported on the table 22), the center of mass including the suspension unit 26 can still be made to lie very close to the first horizontal axis 20, with the addition of little or no counterweight. This preferred positioning of the apparatus also facilitates servicing of the apparatus, since access to the acceleration chamber 34 can easily be gained by bringing the source 12 to a position such that the radiation axis 16 is horizontal and lifting the top cover (not shown).

The mounting unit 18 in the embodiment of FIG. 1 includes a pair of trunnions 42 respectively positioned on opposite sides of the source 12 and coaxial with the first horizontal axis 20. The tunnions 42 are carried by stanchions 42'.

The suspension unit 26 comprises means such as a frame 44 connected to the table 22 and at least one arm such as the arms 46 rigidly connected to the source 12 and pivotably connected to the frame 44 on the second horizontal axis 28.

In another embodiment of the invention, as shown in FIG. 5, two parallel, circular mounting rings 48 are concentric with each other and concentric with the first horizontal axis 20. The source 12 is carried between the rings 48 and rigidly connected for example to spokes 48a. Teeth forming racks 49 may be provided on the outer periphery of each ring 48, and two pairs of pinion gears 50 are respectively engaged with the racks 49 and rotatable in synchronism about fixed, parallel, horizontal shafts in order to orient the source 12 in a desired direction. The rings 48 support a frame 44 therebetween in such a manner such that the radiation axis 16 intersects the second horizontal axis 28. Alternatively, the outer periphery of each ring 48 may be smooth, and the pinion gears 50 may be replaced by smooth rollers. The rings 48 can then be driven synchronously by a separate gear train.

Figure 6:
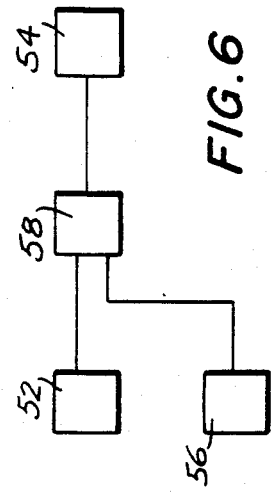
FIG. 6 is a schematic view of apparatus useful in stabilizing a portion of the apparatus of FIGS. 1 or 5.

Whether cantilever arms 46 or rings 48 are employed, the suspension may further comprise a large gyroscopic stabilizer 51 (FIG. 2) connected directly or indirectly to the table 22 for maintaining, by virtue of its directional inertia, a fixed angular position of the table 22 with respect to the environment. Alternatively, as shown in FIG. 6, the suspension 26 may comprise a small gyroscope 52 supported in a mounting rigid with the table 22 for determining the angular position of the table 22 with respect to the environment and a reversible motor 54 connected to the suspension unit 26 and the table 22. A reference signal generator 56 generates a reference signal which is compared by a comparator 58 with a signal generated by the gyroscope 52. The comparator 58 generates an output signal which is employed to control the direction of rotation of the reversible motor 54 in such a manner as to maintain the table 22 with its top surface level or in another fixed angular position with respect to the environment.

In the case where cantilever arms or a pair of rings are employed as a suspension, counterweights 60 (FIG. 2) constituting a pendulum may be connected directly or indirectly to the table 22 for maintaining the top surface of the table level or in another fixed angular position with respect to the environment. A damper 62 may be provided for damping oscillations of the pendulum 60. The damper 62 may for example comprise one or more hydraulic shock absorbers. The shock absorbers can be connected directly or indirectly to the table 22 and to the arm 46 or ring 48 in order to damp relative movement therebetween.

Figure 11:
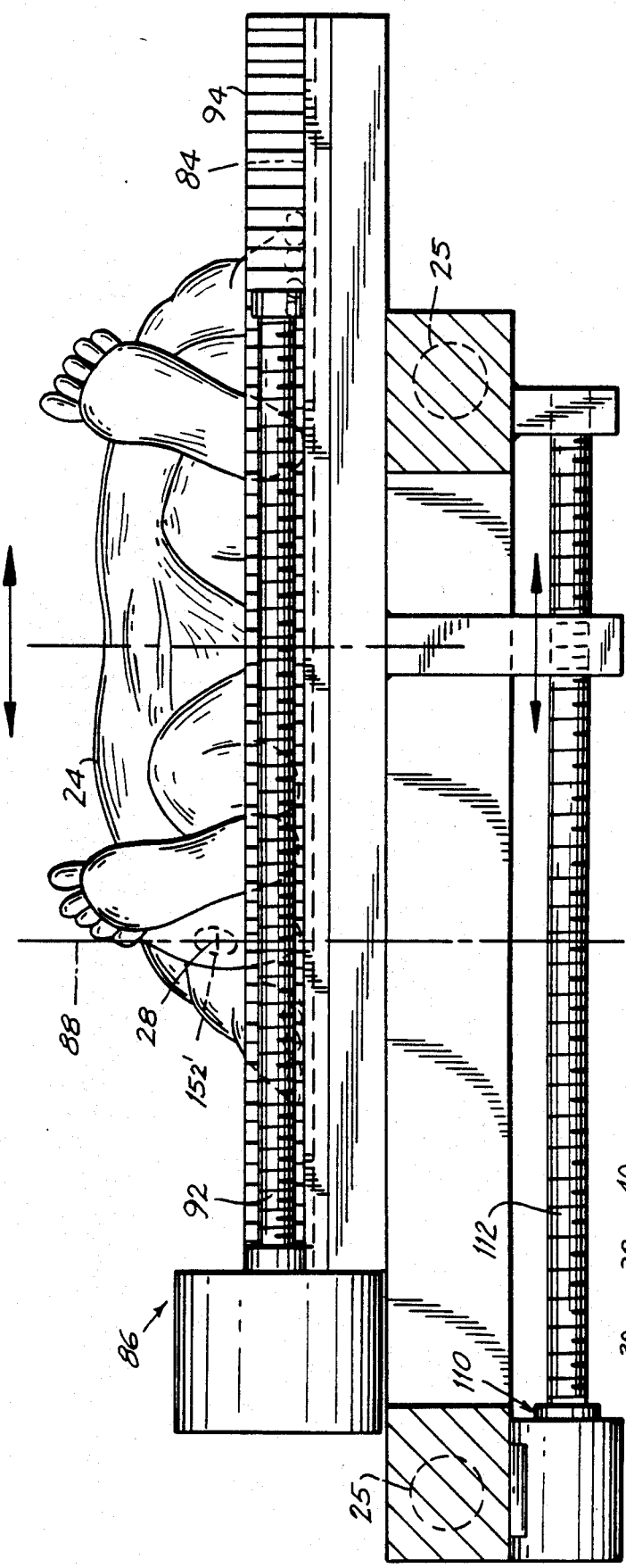
FIG. 11 is a view taken along the line 11—11 of FIG. 2 and looking in the direction of the arrows.

The counterweights 60 are preferably movable in a lateral direction (i.e., the direction having a component parallel to a horizontal line normal to the axes 28), so that the counterweights are adapted to bring the table 22 to a position such that its top surface 84 (FIG. 11) is horizontal, notwithstanding the positioning of the patient in any of a plurality of lateral positions. The movemert of the counterweights 60 is done manually or automatically during the adaptation period.

As another alternative, the suspension unit 26 may comprise a parallelogram structure 64 (FIG. 7) including a pair of arms 66 and 67. The arm 66 is connected rigidly to the source 12 and pivotably to the frame 44. The parallelogram structure 64 includes means such as a gear train 68 connecting the two arms 66, 67 of the pair of arms in a manner such that rotation of one of the arms through a given angle causes rotation of the other of the arms through the same angle, thereby reducing play in the parallelogram structure 64 and improving the precision of its operation. The gear train 68 comprises a first sun gear 70 concentric with the first horizontal axis 20, a second sun gear 72 concentric with a third horizontal axis 74 displaced from and parallel to the first and second horizontal axes 20, 28, and a cogwheel 76 engaged with the first and second sun gears 70, 72. The first sun gear 70 is rigidly connected with the source 12 and first arm 66 and the second sun gear 72 is rigidly connected with the other arm 67. A motor drives any of the gears in the gear train 68, and preferably drives the cogwheel 76.

An arm 78 is parallel to the line connecting the first and third horizontal axes 20 and 74. The arm 80 is pivotable with respect to the arm 67 about a horizontal axis 80 and with respect to the arm 66.

A pair of parallelogram structures 64 may be respectively connected at opposite ends of the table 22, thereby further reducing play in the apparatus and improving precision of its operation.

The suspension 26 may optionally include at one or both ends thereof multiple parallelogram structures 81 as in FIGS. 8 and 9. As FIG. 8 shows, such a multiple parallelogram structure 81 includes at least three arms 81a, 81b and 81c. The arm 81a is rigidly connected to the source 12 and pivots about at a point 82a which is on the first horizontal axis 20, and the arms 81b and 81c are pivotably connected to the mounting means 18 at points 82b and 82c, respectively. The first points 82c, 82a, 82b form a first angle a about the first horizontal axis 20. The arm 81a is pivotably connected to the frame 44 at point 82d. The arms 81b and 81c are pivotably connected to arms 81d and 81e at points 82e and 82f, respectively. The point 82d lies on the second horizontal axis 28, and the second points 82f, 82d, 82e form a second angle a about the second horizontal axis 28. The first and second angles a are equal and oriented in the same direction. Preferably, each of the first and second angles a is substantially 90°.

As FIG. 9 shows, it is not necessary that one arm (the arm 81a in FIG. 8) be common to two parallelograms. In FIG. 9, the arms of the parallelogram having vertices 83a, 83b, 83c, 83d are entirely separate from the lines of the parallelogram having vertices 83e, 83f, 83g, 83h.

In the structures of both FIGS. 8 and 9, the fixed angle discussed above between given arms of two parallelograms ensures that at least one of the parallelograms will be configured in such a manner as to have a substantial moment arm for control of the angular position of the table 22. In the structure of FIG. 7, as the angle a' between the arm 66 and a line connecting the axes 20 and 74 approaches zero, the moment arm likewise approaches zero, so that the gear train 68 becomes a useful supplement.

FIG. 10 shows an embodiment of the invention wherein the separation between the first horizontal axis 20 and the axis 74 exceeds the length of the arms 66 and 67, thereby preventing interference of the arms 66 and 67 with each other in the case of rotation of the source 12 and parallelogram structure through large arcs and in fact making it possible for the parallelogram structure and the source 12 to rotate through a full 360°.

The suspension unit 26 may mount the table 22 for arcuate movement through an angle at least slightly in excess of 90°, 180° or 360°. The advantage of arcuate movement through 360° is clear: it is possible to irradiate a recumbent patient at any azimuthal angle without repositioning the patient on the table 22.

The advantage of arcuate movement through only 180° is that space is saved in that the room in which the apparatus is installed need not accommodate the suspension unit 26 and table 22 over the eliminated portion of the arc. For example, where the upper half of the arc is eliminated and the lower half is retained, the minimum required ceiling height is reduced. Moreover, the patient is never more than, say, two meters above the floor, thereby facilitating retrieval of the patient in the event of power failure. All azimuthal angles with respect to the patient can be covered by positioning the patient alternately in the supine and prone positions. It is also possible, in the case of arcuate movement through only 180°, to save floor space by eliminating the left (or right) portion of the arc and retaining the right (or left) portion. All azimuthal angles with respect to the patient can be moved by positioning the patient alternately in the "head north" and "head south" positions.

The advantage of arcuate movement through only 90° is that still more space is saved. For example, the fourth quadrant of the arcuate movement (FIG. 3) may be retained and the first through third quadrants eliminated. This reduces both the minimum required ceiling height and the minimum required floor space. It also ensures that the patient is never more than, say, two meters above the floor, thereby facilitating retrieval of the patient in the event of power failure. All azimuthal angles with respect to the patient can be covered by arranging the patient in any of four positions: supine, "head north"; supine, "head south"; prone, "head north"; and prone, "head south".

In the event of power failure with the patient in an elevated position, retrieval of the patient in the case of any of the embodiments of the invention can be accomplished by means of a battery-powered vehicle V (FIG. 3A, drawn on a somewhat smaller scale than FIG. 3) having an elevating platform P. Such a vehicle should be kept out of but adjacent to the radiation room so that on the one hand it does not become radioactive but on the other hand it is available for immediate use in the event of a power or control failure or the like with the patient in an elevated position.

The table 22 is preferably formed with a substantially flat upper surface 84 (FIG. 11) for supporting the patient 24, and the suspension unit 26 maintains the flat surface 84 in a substantially horizontal plane.

Figure 12:
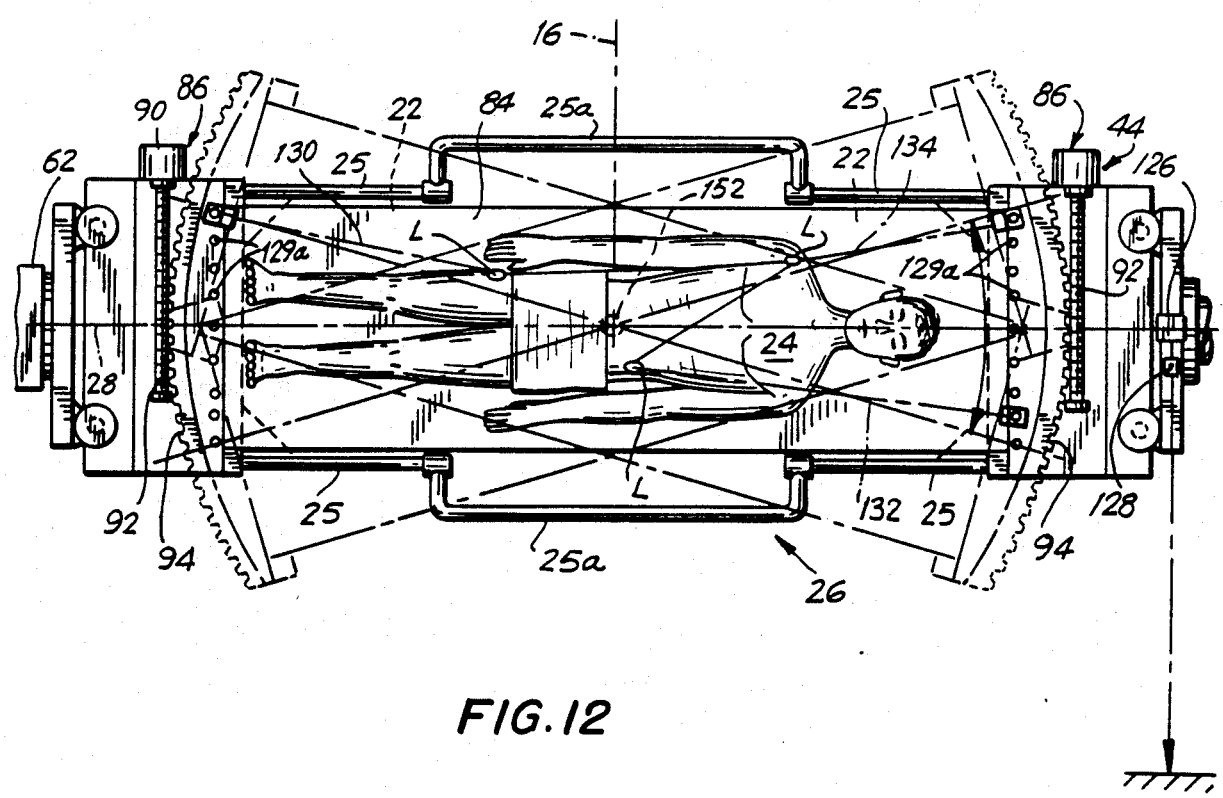
FIG. 12 is a view taken along the line 12—12 of FIG. 2 and looking in the direction of the arrows.

The suspension unit 26 comprises means 86 (FIGS. 2 and 12) for pivoting the table 22 about a vertical axis 88 intersecting the radiation axis 16 and the second horizontal axis 28, whereby the radiation axis 16 can be made to intersect the body of a patient 24 lying supine or prone at different angles about the anterior-posterior axis of the patient. This may make it possible for example to avoid irradiating a kidney or other organ especially sensitive to radiation when irradiating a nearby tumor. The pivoting means may comprise for example a motor 90 driving a worm 92 which engages a sector gear 94 concentric with the vertical axis 88 and rigidly attached to the frame. This permits orientation of the table 22 at different angles as best shown in FIG. 12.

The suspension unit 26 also comprises means 96 (FIG. 2) for moving the table 22 in a vertical direction with respect to the suspension unit 26, whereby the radiation axis 16 can be made to intersect the body of a patient 24 at different heights above the surface of the table 22. The means for effecting the vertical movement comprises screws 98 at either end of the table 22 connected directly or indirectly to the table 22.

The suspension unit 26 comprises means 102 for moving the table 22 in a direction parallel to the horizontal axes 20 and 28, whereby the radiation axis 16 can be made to intersect the body of a patient 24 at different locations along the length of the patient. The means 102 can comprise for example a screw 104 driven by an electric motor.

Alternatively, or in addition, the table 22 may have a length exceeding the length of the patient 24, which makes it possible to adapt the patient to the table 22 in such a way that the radiation axis 16 can be made to intersect the body of the patient 24 at different locations along the length of the patient.

The suspension 26 comprises means such as a drive 110 (FIG. 11) for moving the table 22 in a direction parallel to a horizontal line which is normal to either of the horizontal axes 20 and 28, whereby the radiation axis 16 can be made to intersect the body of a patient 24 at different locations along the width of the patient. The drive 110 comprises screws 112 at either end of the table 22 and each driven an electric motor.

Alternatively, or in addition, the table 22 may have a width exceeding the width of the patient 24, which makes it possible to adapt the patient to the table 22 in such a way that the radiation axis 16 can be made to intersect the body of the patient 24 at different locations along the width of the patient. The table 22 should not be excessively wide, however, since excessive table width would hinder nurses or other personnel in adapting the patient to the table 22 and necessitate an excessive separation between the patient and the source 12.

The suspension 26 further includes calibrating means 116 (FIG. 3) for measuring the angular position of the table 22, thereby enabling detection and correction of an error between the angular position of the table 22 and a desired angular position. The calibrator 116 comprises for example optical means for generating first and second optical beams 118, 120 at an angle b, preferably 90°, with respect to each other and screens 122, 124 for intercepting the first and second optical beams 118, 120 at first and second points 126, 128 respectively. The screens 122, 124 may be similar to those used for projection in motion picture theaters or may simply be the walls, ceiling and floor of the room in which the apparatus is located. As the source 12 rotates about the first horizontal axis 20, the second horizontal axis 28 and therefore the calibrator 116 move correspondingly. Thus the points 126 and 128 move, for example to points 126' and 128' as illustrated in the 90-degree position in FIG. 3. Means is provided for correlating the first and second points 126, 128 or 126', 128', etc., and the angular position of the radiation axis 16 with the angular position of the table 22. For example, for every angular position of the radiation axis 16 there is a unique set of points 126, 128 which corresponds to a horizontal top surface 84 of the table 22. Thus if for a given angular position of the radiation axis 16 the point 126 is higher than a reference value and the point 128 is to the left of a reference value, the table 22 is tilted counterclockwise (FIG. 3) from its level position. Means can then be provided, including for example the apparatus of FIG. 6, for reorienting the table 22 about the second horizontal axis 28 in such a manner as to bring the surface 84 into the desired reference plane. A third beam, preferably at right angles to the beams 118 and 120, can be provided if desired for greater convenience and precision of measurement.

The optical device for generating the beams 118 and 120 preferably comprises a laser 126 (FIG. 12) and beam splitter 128 so that the optical beams are laser beams. It is of course possible to provide screens similar to 122 and 124 on the left of the source 12 as seen in FIG. 3 and also below the source (for example on the floor).

The suspension unit 26 also comprises means for detecting inadvertent minor movements by the patient with respect to the table 22 during the actual irradiation and means for adjusting the position of the table 22 in such a manner as to return the patient to a prescribed position with respect to the radiation beam 14. The detector comprises optical means, preferably laser means, mounted on poles 129 adjustably positioned in holes 129a for generating at least one and optionally two or three optical beams 130, 132, 134 (FIG. 2), preferably laser beams, directed towards the patient. Where multiple beams are employed, they preferably travel in three different directions and impinge on the patient in different locations. Where three beams are employed, the locations L where they intersect the patient, if not in a straight line, define a triangle. During the adaptation period, each such location is marked with reference means such as a photocell, an adhesive patch or a dab of paint. Preferably locations are selected that are not too far from the site of the tumor. In certain cases it may be advantageous to select locations that do not move appreciably when the patient breathes.

During the irradiation period, it is virtually impossible for the patient to move without displacing at least one of the photocells, adhesive patches or dabs of paint relative to the location at which the associated beam impinges on the patient. Such displacement can be indicated automatically if photocells are employed, and an alarm can thus be sounded. FIG. 14 shows a suitable circuit for this purpose. The three photocells 136, 138, 140 have their respective outputs connected to the respective input terminals of an AND-gate 142. As long as all three photocells produce an output, the AND gate produces an output. If because of displacement of a laser beam with respect to the reference location of impingement on the patient any photocell 136, 138 or 140 fails to produce an output, the AND-gate 142 fails to produce an output. An inverter 144 connected to the output of the AND gate 142 then produces an output that activates an alarm 146. Alternatively, the displacement can be indicated visually by means of a television camera 148 mounted in the radiation room and a monitor 150 mounted outside but adjacent to the radiation room, as illustrated in FIG. 13.

In either case, when minor movement of the patient is detected, the patient is returned to the correct position by activating the appropriate motor or motors described above to translate the table 22 longitudinally, transversely and/or in elevation, and/or to rotate the table about the vertical axis, as may be required. Of course, if the patient moves in a major way, as by rolling over or sitting up, correction in this manner is not possible, and the irradiation of the patient must be immediately terminated.

The method of the invention for irradiating a tumor 152 comprises the steps of providing a source 12 of a radiation beam 14 directed along a radiation axis 16, providing a table 22 having a substantially flat upper surface 84 for supporting a patient 24, positioning a patient 24 on the surface 84 so that the radiation axis 16 intersects the tumor 152 at a first angle, rotating the radiation axis 16 about a first horizontal axis 20 and simultaneously moving the table 22 so that the radiation axis 16 intersects the tumor 152 at a second angle while pivoting the table 22 about a second horizontal axis 28 displaced from and substantially parallel to the first horizontal axis 20 to maintain the surface 84 substantially level, and irradiating the tumor 152 at the second angle.

The patient preferably assumes a recumbent position, which may be supine or prone. The irradiating steps employ charged particles, neutrons or photons. The tumor can be irradiated in separate treatment sessions, while preserving the option of irradiating the tumor from two or more different angles in a single session. If two or more irradiating steps are performed in a single treatment session, the patient remains on the table 22, which is simply rotated from one angular position about the first horizontal axis 20 to another, while being maintained level or in another fixed angular position with respect to the environment. If the irradiating steps are performed in separate treatment sessions, the patient may be dismissed between sessions and may return one or more days later, for example, for the second irradiating step.

Similar sessions may be scheduled over a period of weeks as indicated by the regression of the tumor. The different angles employed maximize the probability of weakening and ultimately killing the cancer cells while minimizing the damage to normal cells so that they can be expected to recover.

The method of the present invention also facilitates what may be described as "arc therapy". Much of the time required by a session is for proper adaptation of the patient. During the adaptation period, the patient is properly positioned on the table 22, instructed or reminded to lie as still as possible during the actual radiation, etc. The adaptation period may require 20 minutes, for example. It may be physiologically undesirable to irradiate a patient at a given angle for more than, say, three minutes, because of the risk of unacceptable injury to normal cells, yet physiologically acceptable to irradiate the patient for, say, three minutes at a first angular position, three minutes at a second angular position removed from the first angular position by 90°, plus a minute or fraction thereof required for moving from the first angular position to the second. At the first angular position, the second angular position, and during the transition between the two, the radiation axis intersects the tumor, with no further adaptation of the patient. This substantially improves the ratio of radiation time to adaptation time, thereby reducing the number of sessions required, and making it possible to treat more patients per machine. Since the cost of the machine is amortized over a larger patient base, the cost of treating each patient is reduced.

Thus there is provided in accordance with the invention a novel and highly-effective method and apparatus for the treatment of cancer patients. In accordance with the invention, it is possible to ascertain the position of the tumor with respect to a radiation beam to a high degree of accuracy, notwithstanding movement of the table 22 to a plurality of angular positions about a radiation source. The apparatus is designed so that it weighs and costs significantly less than conventional apparatus. It can employ a cyclotron as the radiation (whether or not the coils for generating the magnetic field are superconducting), a synchro-cyclotron having superconducting coils for generating the magnetic field, a synchrotron having superconducting coils for generating the magnetic field, or a microtron. The apparatus requires little or no counterweight, since the first horizontal axis 20 passes substantially through the center of mass of the apparatus; yet is fully adapted to irradiate a patient from a different angles. The apparatus is easy and inexpensive to service, since access to the acceleration chamber can easily be gained by bringing the source 12 to a position such that the radiation axis 16 is horizontal and lifting the top cover (not shown). The method of the invention facilitates the irradiation of a tumor with great precision from different angles.

Many modifications of the preferred embodiments of the invention disclosed herein will readily occur to those skilled in the art. For example, the intensity of the radiation source, the cross-sectional area of the radiation beam, the duration of each radiation session, the interval between radiation sessions, the number of such sessions, etc., can be varied within wide limits. Accordingly, the invention includes all structure and methods that fall within the scope of the appended claims.

I claim:

1. Apparatus for irradiating a patient and comprising:
   a source of a radiation beam directed along a radiation axis;
   means mounting said source for pivotal movement about a first horizontal axis which intersects said source, is stationary with respect to said apparatus, and extends in a direction substantially normal to said radiation axis, whereby said beam is capable of an angular scan in a vertical plane;
   table means adapted to support a patient to be irradiated; and
   suspension means mounted said table means for arcuate movement to any of a plurality of positions angularly spaced about said first horizontal axis and for pivoting movement about a second horizontal axis displaced from and substantially parallel to said first horizontal axis, said suspension means maintaining said second horizontal axis in substantially intersecting relation to said radiation axis in each of said positions while maintaining a fixed angular position of said table means with repsect to the environment.

2. Apparatus according to claim 1; wherein said source comprises a cyclotron.

3. Apparatus according to claim 2; wherein said cyclotron has superconducting coils for generating the magnetic field.

4. Apparatus according to claim 1; wherein said source comprises means for accelerating charged particles and an internal target, said charged particles hitting said target, thereby generating said radiation beam and said apparatus being positioned so that said horizontal axis intersects said target.

5. Apparatus according to claim 1; wherein said source comprises a synchro-cyclotron having superconducting coils for generating the magnetic field.

6. Apparatus according to claim 1; wherein said source comprises a synchrotron having superconducting coils for generating the magnetic field.

7. Apparatus according to claim 1; wherein said source comprises a microtron.

8. Apparatus according to any one of claims 2–7; wherein said source comprises means including spaced-apart pole surfaces for generating a magnetic field, said apparatus being positioned so that the midplane between said pole surfaces substantially includes said first horizontal axis.

9. Apparatus according to claim 1; wherein said mounting means comprises a pair of trunnions.

10. Apparatus according to claim 1; wherein said suspension means comprises frame means connected to said table means and an arm rigidly connected to said source and pivotably connected to said frame means on said second horizontal axis.

11. Apparatus according to claim 1; wherein said suspension means comprises frame means connected to said table means and a pair of circular rings concentric with each other and with said first horizontal axis and means mounting said rings for synchronous rotation, said rings supporting said frame means therebetween.

12. Apparatus according to claim 10 or 11; wherein said suspension means further comprises gyroscopic stabilizing means connected to said table means for maintaining said fixed angular position of said table means with respect to the environment.

13. Apparatus according to claim 10 or 11; wherein said suspension means further comprises gyroscopic means for determining the angular position of said table means with respect to the environment and motor means connected to said frame means and said table means, said gyroscopic means controlling the operation of said motor means in such a manner as to maintain said fixed angular position of said table means with respect to the environment.

14. Apparatus according to claim 10 or 11; wherein said suspension means further comprises pendulum means rigidly connected to said table means for maintaining said fixed angular position of said table means with respect to the environment.

15. Apparatus according to claim 14; further comprising damper means for damping oscillations of said pendulum means.

16. Apparatus according to claim 1; wherein said suspension means comprises frame means connected to said table means and a parallelogram structure including a pair of arms, one of said arms being rigidly connected to said source and pivotably connected to said frame means and the other of said arms being pivotably connected to said mounting means and said frame means.

17. Apparatus according to claim 16; wherein said parallelogram structure includes gear means connecting the two arms of said pair of arms in such a manner that rotation of said one arm through a given angle causes rotation of said other arm through the same angle, thereby reducing play in said parallelogram structure and improving the precision of its operation.

18. Apparatus according to claim 17; wherein said gear means comprises a first sun gear concentric with said first horizontal axis, a second sun gear concentric with a third horizontal axis displaced from and parallel to said first and second horizontal axes, and a cogwheel engaged with said first and second sun gears, said first sun gear being rigidly connected with said one arm and said second sun gear being rigidly connected with said other arm.

19. Apparatus according to claim 1; wherein said suspension means comprises frame means connected to said table means and a pair of parallelogram structures respectively connected at opposite ends of said table means, each parallelogram structure including a pair of arms, one arm of each pair being rigidly connected to said source and pivotably connected to said frame means and the other arm of each pair being pivotably connected to said mounting means and said frame means.

20. Apparatus according to claim 1; wherein said suspension means comprises frame means connected to said table means and multiple parallelogram means, said multiple parallelogram means including at least three arms, said arms being connected respectively to said source and said mounting means at first points forming a first angle about said first horizontal axis and to said frame means at second points forming a second angle about said second horizontal axis, said first and second angles being equal and oriented in the same direction.

21. Apparatus according to claim 20; wherein each of said first and second angles is substantially 90°.

22. Apparatus according to claim 1; wherein said suspension means comprises frame means connected to said table means and a parallelogram structure including a pair of arms, one of said arms being rigidly connected to said source and pivotably connected to said frame means and the other of said arms being pivotably connected to said mounting means and said frame means, and the separation between said arms being sufficient to enable rotation thereof through 360°.

23. Apparatus according to claim 1; wherein said table means is formed with a substantially flat upper surface for supporting a patient and said suspension means maintains said flat surface in a substantially horizontal plane.

24. Apparatus according to claim 1; wherein said suspension means mounts said table means for arcuate movement through an angle at least slightly in excess of 90°.

25. Apparatus according to claim 1; wherein said suspension means mounts said table means for arcuate movement through an angle at least slightly in excess of 180°.

26. Apparatus according to claim 1; wherein said suspension means mounts said table means for arcuate movement through an angle at least slightly in excess of 360°.

27. Apparatus according to claim 1; further comprising a battery-powered vehicle having an elevating platform and facilitating retrieval of the patient in the event of a power or control failure with the patient in an elevated position.

28. Apparatus for irradiating a patient and comprising:
  a source of a radiation beam directed along a radiation axis;
  means mounting said source for pivotal movement about a first horizontal axis substantially normal to said radiation axis, whereby said beam is capable of an angular scan in a vertical plane;
  table means adapted to support a patient to be irradiated; and
  suspension means mounting said table means for arcuate movement to any of a plurality of positions angularly spaced about said first horizontal axis and for pivoting movement about a second horizontal axis displaced from and substantially parallel to said first horizontal axis, said suspension means maintaining said second horizontal axis in substantially intersecting relation to said radiation axis in each of said positions while maintaining a fixed angular position of said table means with respect to the environment;

wherein said suspension means comprises means for pivoting said table means about a vertical axis intersecting said radiation axis and said second horizontal axis, whereby said radiation axis can be made to intersect the body of a patient lying supine or prone at different angles about the anterior-posterior axis of the patient.

29. Apparatus according to claim 1; wherein said suspension means comprises means for moving said table means in a vertical direction with respect to said suspension means, whereby said radiation axis can be made to intersect the body of a patient at different heights above the surface of said table means.

30. Apparatus according to claim 1; wherein said suspension means comprises means for moving said table means in a direction parallel to said first and second horizontal axes, whereby said radiation axis can be made to intersect the body of a patient at different locations along the length of the patient.

31. Apparatus according to claim 1; wherein said table means has a length exceeding the length of the patient, which makes it possible to adapt the patient to said table means in such a way that said radiation axis can be made to intersect the body of the patient at different locations along the length of the patient.

32. Apparatus according to claim 1; wherein said suspension means comprises means for moving said table means in a direction parallel to a horizontal line which is normal to one of said horizontal axes; whereby said radiation axis can be made to intersect the body of a patient at different locations along the width of the patient.

33. Apparatus according to claim 1; wherein said table means has a width exceeding the width of the patient, which makes it possible to adapt the patient to said table means in such a way that said radiation axis can be made to intersect the body of a patient at different locations along the width of the patient.

34. Apparatus according to claim 1; wherein said suspension means comprises calibrating means for measuring said fixed angular position, thereby enabling detection and correction of an error between said fixed angular position and a desired angular position.

35. Apparatus according to claim 34; wherein said calibrating means comprises optical means for generating first and second optical beams at an angle with respect to each other, screen means for intercepting said first and second optical beams at first and second points, respectively, and means for correlating said first and second points and a selected one of said plurality of positions with said desired angular position.

36. Apparatus according to claim 35; wherein said optical means comprises a laser and said optical beams are laser beams.

37. Apparatus according to claim 35; wherein said angle between said first and second optical beams is substantially 90°.

38. Apparatus according to claim 1; wherein said suspension means comprises detector means for detecting movement of the patient with respect to said table means and drive means for adjusting the position of said table means in such a manner as to return the patient to a prescribed position with respect to said radiation beam.

39. Apparatus according to claim 38; wherein said detector means comprises optical means for generating an optical beam directed towards the patient, reference means positioned on the patient at a location at which said beam impinges when said patient is properly positioned on said table means, and means for indicating displacement of said beam from said location.

40. Apparatus according to claim 39; wherein said optical means comprises a laser and said optical beam is a laser beam.

41. Apparatus according to claim 39; wherein said optical means generates a plurality of optical beams directed towards the patient, said beams traveling in different directions and impinging on the patient in different locations.

42. Apparatus according to claim 39; wherein said optical means generates three optical beams directed towards the patient, said beams travelling in three different directions and impinging on the patient in three different locations defining a triangle.

43. Apparatus according to claim 39; wherein said reference means comprises a photocell positioned at said location and said indicator means comprises means responsive to said photocell for activating an alarm in case of displacement of said beam from said location.

44. Apparatus according to claim 39; wherein said optical means generates a plurality of optical beams directed towards the patient, said beams impinging of the patient in a plurality of locations, said reference means comprises a plurality of photocells respectively positioned at said locations, and said indicator means comprises means responsive to said photocells for activating an alarm in case of displacement of any of said beams from said respective locations.

45. Apparatus according to claim 39; wherein said reference means comprises an adhesive patch positioned at said location and said indicator means comprises a television camera and monitor.

46. Apparatus according to claim 39; wherein said reference means comprises a dab of paint positioned at said location and said indicator means comprises a television camera and monitor.

47. Apparatus for irradiating a patient and comprising:
a source of a radiation beam directed along a radiation axis;
means mounting said source for pivotal movement about a first horizontal axis substantially normal to said radiation axis, whereby said beam is capable of an angular scan in a vertical plane;
table means adapted to support a patient to be irradiated; and
suspension means mounting said table means for arcuate movement to any of a plurality of positions angularly spaced about said first horizontal axis and for pivoting movement about a second horizontal axis displaced from and substantially parallel to said first horizontal axis, said suspension means maintaining said second horizontal axis in substantially intersecting relation to said radiation axis in each of said positions while maintaining a fixed angular position of said table means with respect to the environment;
wherein said suspension means comprises detector means for detecting movement of the patient with respect to said table means and drive means for adjusting the position of said table means in such a manner as to return the patient to a prescribed position with respect to said radiation beam; and
wherein said drive means comprises means for translating said table means longitudinally, means for translating said table means transversely, means for translating said table means in elevation, and means for rotating said table about a vertical axis intersecting said radiation axis and said second horizontal axis.

48. A method of irratiating a tumor comprising the steps of:
   providing a source of radiation beam directed along a radiation axis;
   providing a table having a substantially flat upper surface for supporting a patient;
   positioning a patient on said surface so that said radiation axis intersects said tumor at a first angle;
   irradiating said tumor at a first angle;
   rotating said radiation axis about a first horizontal axis which intersects said source while maintaining said first horizontal axis stationary and simultaneously moving said table so that said radiation axis intersects said tumor at a second angle while pivoting said table about a second horizontal axis displaced from and substantially parallel to said first horizontal axis to maintain said surface substantially level; and
   irradiating said tumor at said said second angle.

49. A method according to claim 48; wherein the patient assumes a recumbent position.

50. A emthod according to claim 48; wherein the patient assumes a supine position.

51. A method according to claim 48; wherein the patient assumes a prone position.

52. A method according to claim 48; wherein said irradiating steps employ charged particles.

53. A method according to claim 48; wherein said irradiating steps employ neutrons.

54. A method according to claim 48; wherein said irradiating steps are performed in a single treatment session.

55. A method according to claim 48; wherein said irradiating steps are performed in a single treatment session, further comprising the step of irradiating said tumor during said rotating of said radiation axis.

56. A method according to claim 48; wherein said irradiating steps are performed in separate treatment sessions.

57. A method of irradiating a tumor comprising the steps of:
   providing a source of a radiation beam directed along a radiation axis;
   providing a table having a substantially flat upper surface for supporting a patient;
   positioning a patient on said surface so that said radiation axis intersects said tumor at a first angle;
   irradiating said tumor at said first angle;
   rotating said radiation axis about a first horizontal axis and simultaneously moving said table so that radiation axis intersects said tumor at a second angle while pivoting said table about a second horizontal axis displaced from and substantially parallel to said first horizontal axis to maintain said surface substantially level; and
   irradiating said tumor at said second angle;
   further comprising the step of pivoting said table about a vertical axis intersecting said radiation axis and said second horizontal axis, whereby said radiation axis intersects said tumor at different angles about the anterior-posterior axis of a patient lying supine or prone.

* * * * *